United States Patent
Lavin Carrasco

(10) Patent No.: US 10,570,022 B2
(45) Date of Patent: Feb. 25, 2020

(54) MICROSTRUCTURED MULTICOMPOSITE COPPER MICROPARTICLE WITH ANTIBACTERIAL AND/OR BIOCIDAL ACTIVITY THAT COMPRISES IN ITS STRUCTURE 5 DIFFERENT TYPES OF COPPER COMPOUNDS, ALL REGULAR AND CRYSTALLINE

(71) Applicant: COPPERPROTEK SPA, Las Condes (CL)

(72) Inventor: Javier Ignacio Lavin Carrasco, Santiago (CL)

(73) Assignee: COPPERPROTEK SPA, Las Condes (CL)

(*) Notice: Subject to any disclaimer, the term of this patent is extended or adjusted under 35 U.S.C. 154(b) by 0 days.

(21) Appl. No.: 16/358,384

(22) Filed: Mar. 19, 2019

(65) Prior Publication Data
US 2019/0367380 A1 Dec. 5, 2019

Related U.S. Application Data

(63) Continuation of application No. PCT/IB2018/053819, filed on May 29, 2018.

(51) Int. Cl.
*A61L 9/00* (2006.01)
*A61L 9/01* (2006.01)
(Continued)

(52) U.S. Cl.
CPC .............. *C01G 3/10* (2013.01); *A01N 59/20* (2013.01); *C08J 3/22* (2013.01); *C08K 3/30* (2013.01);
(Continued)

(58) Field of Classification Search
CPC .............. A01N 59/20; B05D 1/02; B22F 1/02
(Continued)

(56) References Cited

U.S. PATENT DOCUMENTS 2,551,446 A 5/1951 Clay
5,458,906 A 10/1995 Liang
(Continued)

FOREIGN PATENT DOCUMENTS

| CL | 201500921 | 10/2015 |
| CL | 201503652 | 12/2015 |

(Continued)

OTHER PUBLICATIONS

Betancourt, R. et al., "Antimicrobial Chemicals Are Associated with Elevated Antibiotic Resistance Genes in the Indoor Dust Microbiome", Environmental Science & Technology, 2016, vol. 50, pp. 9807-9815.
(Continued)

*Primary Examiner* — Monzer R Chorbaji
(74) *Attorney, Agent, or Firm* — Gorman IP Law, APC

(57) ABSTRACT

A copper microparticle with antibacterial and/or biocidal activity, wherein each microparticle has a regular, crystalline and microstructured composition that comprises 5 different copper compounds: Antlerite $Cu_3^{+2}(SO_4)(OH)_4$, Brochantite $Cu_4^{+2}SO_4(OH)_6$, Chalcantite $Cu^{+2}SO_4.5H_2O$, Natrochalcite $NaCu_2^{+2}(SO_4)_2OH.H_2O$ and Hydrated copper sulfate hydroxide $Cu_3(SO_4)_2(OH)_2.4H_2O/2CuSO_4.Cu(OH)_2$, with the microparticle having a size of between 5 and 50 μm. A process for preparing copper microparticles with antibacterial and/or biocidal activity. A concentrated polymeric composition (masterbatch) with antibacterial and/or biocidal activity that is incorporated during the extrusion process to molten polymers for forming rigid or flexible products such as fibers, filaments, and sheets. A use of a copper micropar-
(Continued)

a)

b)

c)

d)

ticle with antibacterial and/or biocidal activity. A use of a concentrated polymeric composition (masterbatch) with antibacterial and/or biocidal activity.

15 Claims, 3 Drawing Sheets

(51) Int. Cl.
| | |
|---|---|
| *A01N 55/02* | (2006.01) |
| *C09K 3/00* | (2006.01) |
| *C01G 3/10* | (2006.01) |
| *C08K 3/30* | (2006.01) |
| *A01N 59/20* | (2006.01) |
| *C08J 3/22* | (2006.01) |

(52) U.S. Cl.
CPC ...... *C01P 2002/72* (2013.01); *C01P 2004/03* (2013.01); *C01P 2004/61* (2013.01); *C01P 2004/82* (2013.01); *C08J 2309/06* (2013.01); *C08J 2323/06* (2013.01); *C08J 2323/08* (2013.01); *C08J 2323/12* (2013.01); *C08J 2325/06* (2013.01); *C08J 2327/18* (2013.01); *C08J 2333/10* (2013.01); *C08J 2367/02* (2013.01); *C08K 2003/3045* (2013.01); *C08K 2201/005* (2013.01)

(58) Field of Classification Search
USPC ...... 514/499; 422/28; 252/389.61; 424/76.8, 424/76.9, 622, 630; 106/733
See application file for complete search history.

(56) References Cited

U.S. PATENT DOCUMENTS

| | | | |
|---|---|---|---|
| 7,169,402 | B2 | 1/2007 | Gabbay |
| 7,754,625 | B2 | 7/2010 | Hendriks et al. |
| 8,183,167 | B1 | 5/2012 | Delattre et al. |
| 8,911,794 | B2 | 12/2014 | Ferrier et al. |

FOREIGN PATENT DOCUMENTS

| | | | |
|---|---|---|---|
| CN | 100556814 C | 11/2009 | |
| WO | 2000053413 A1 | 9/2000 | |
| WO | 2012127326 A1 | 9/2012 | |
| WO | 2014001541 A1 | 1/2014 | |
| WO | 2014117286 A1 | 8/2014 | |
| WO | 2017113023 A1 | 7/2017 | |
| WO | WO 2017/113023 A1 * | 7/2017 | ............. A01N 59/20 |

OTHER PUBLICATIONS

Chatterjee, A. et al., "Mechaism of antibacterial activity of copper nanoparticles", Nanotechnology, 2014, pp. 1-12.
Delgado, K. et al., "Polypropylene with embedded copper metal or copper oxide nanoparticles as a novel plastic antimicrobal agent", Letters in Applied Microbiology, the Society for Applied Microbiology, 2011, vol. 53, p. 50-54.
International Search Report dated Oct. 30, 2019.
Written Opinion dated Oct. 30, 2019.

* cited by examiner

MICROSTRUCTURED MULTICOMPOSITE COPPER MICROPARTICLE WITH ANTIBACTERIAL AND/OR BIOCIDAL ACTIVITY THAT COMPRISES IN ITS STRUCTURE 5 DIFFERENT TYPES OF COPPER COMPOUNDS, ALL REGULAR AND CRYSTALLINE

This application is a continuation application of PCT Patent Application No. PCT/IB2018/053819, filed internationally on May 29, 2018, the entire contents of which is hereby incorporated by reference.

DESCRIPTION OF THE INVENTION

The present invention relates to a microstructured multicomposite copper microparticle with antibacterial and/or biocidal activity that comprises in its structure 5 different types of copper compounds, all regular and crystalline, that explain the advantageous structural properties of the microparticle: Antlerite $Cu_3^{+2}$ $(SO_4)$ $(OH)_4$, Brochantite $Cu_4^{+2}SO_4$ $(OH)_6$, Chalcantite $Cu^{+2}SO_4.5H_2O$, Natrochalcite $NaCu_2^{+2}(SO_4)_2OH.H_2O$, Copper sulfate hydroxide $Cu_3 (SO_4)_2$ $(OH)_2.4H_2O/2CuSO_4.Cu$ $(OH)_2$. The homogeneous composition of the microstructured multicomposite microparticle enables differential release speed characteristics of each one of the 5 different copper compounds to be uniform throughout the material in which they are incorporated, with each copper compound carrying out its antibacterial and/or biocidal effect individually at the same time in all of the places where the microparticle structure is present. Due to the inclusion of the five copper compounds in the same microstructured microparticle, we have homogeneous and uniform distribution of these compounds, which also enables fewer doses to be used, contributing to the translucent characteristic of the material.

The production process of the microstructured multicomposite microparticle consists in the preparation of a dispersion of copper hydroxide in gel state, which is emulsified with a solution of copper sulfate in water as the solvent, this dispersion/solution is immediately followed by a spray drying process in a hot air flow.

The use of the microparticle in the production of materials with antibacterial and/or biocidal activity is also disclosed.

The scope of the invention also includes a concentrated polymeric composition (masterbatch) which comprises the described microstructured multicomposite copper microparticle and a polymer or resin, which can be included in other/various materials to impart antibacterial and/or biocidal activity to them. Particularly, the masterbatch can be utilized in the structuring of multilayer sheets with antibacterial and/or biocidal activity.

BACKGROUND

Application of copper salts and copper microparticles in polymers and resins for the control of the growth proliferation.

The appearance of multidrug-resistant microorganisms has triggered the search for novel compounds which are capable of combating bacterial proliferation without acquiring resistance as is the case with the agents currently being used (Betancourt et al. 2016).

The development of nanotechnology has permitted the creation of materials which can have dimensions within the order of micrometers and nanometers, materials which show very promising characteristics as antimicrobial agents (Chatterjee et al. 2014). The nano- and microparticles, have the ability to act independently or as transporters of other molecules, and by virtue of their characteristics of surface area, volume, and structure, can trigger biological responses (Chatterjee et al. 2014).

Copper is among the chemical elements used to form nano and microparticles. Copper compounds and complexes have been used in formulations and products for the disinfection of liquids, solids, and human tissues (Delgado et al. 2011).

Different documents from the prior art have described the incorporation of copper compounds and copper nano-/microparticles into solids with the objective of producing a product with antibacterial and/or biocidal properties.

In the case of textile-type materials and fibers, the document U.S. Pat. No. 8,183,167 (B1) discloses fabric substrates which are covalently bonded with copper and/or silver nanoparticles which show antimicrobial activity.

The document U.S. Pat. No. 5,458,906 A presents a method for treating biodegradable substrates with antibacterial compounds, among them, copper. U.S. Pat. No. 7,754,625B2 describes an antimicrobial textile that comprises one or more natural or synthetic fibers or filaments that are combined with an antimicrobial agent, where said antimicrobial agent comprises a predominant quantity of a water-soluble zinc salt in combination with at least one source of antimicrobial silver ions and at least one source of copper ions.

The document U.S. Pat. No. 7,169,402B2 presents an antimicrobial and antiviral polymeric material that has microscopic particles of ionic copper encapsulated in it, which are included in the surface of the product to be formed.

In the document CL201300332 (WO 2014117286 A1) an impregnable matrix of vegetable, animal, or synthetic origin or mixtures thereof in different proportions which contains an antimicrobial compound corresponding to $Cu_4SO_4$ $(OH)_6$ is disclosed.

The document CL201500921 discloses a cellulose-based material that incorporates an antibacterial agent corresponding to a copper compound, mixed copper microparticles or nanoparticles. A method for manufacturing a cellulose-based material which includes steps for the addition of copper microparticles or nanoparticles is included.

The document CL 201503652, in turn, presents a translucent adhesive film which shows surface-protecting antibacterial activity, adhesive film which comprises nanoparticles of copper, chitosan, gelatin, and glutaraldehyde.

Various materials have been developed specifically for the food industry for packaging foods. The documents WO 2014001541 A1, WO 2012127326 A1, and WO 2000053413 A1 describes the production of polymeric materials that contain copper particles for the purpose of use in food packaging with antibacterial and/or biocidal properties. The materials envisaged in these documents include copper compounds or copper particles, with copper oxide primary among them.

Although there are several previous antecedents with reference to the addition of copper compounds and copper microparticles supported on different types of carrier or mixtures of them in matrices and polymeric materials to grant antibacterial properties, the proposals vary with respect to the oxidation state of copper. The oxidation state of the copper will influence the solubility of the kind of copper, and, consequently, in the release behavior thereof from the polymeric material; what is more, the different carriers used tend to make the essential particles bulky.

With regards to antibacterial and/or biocidal materials for packaging or containers, it is necessary to produce quick and instantaneous release in the container to inhibit the surface growth of microorganisms on the foods which cause them to deteriorate and are present at the time of packaging (RAM bacteria). Medium-term release is also necessary to inhibit outbreaks caused by the particular handling of each operation, temperature changes, and storage, among other things. In practice, it is therefore necessary that a material include copper microparticles having a solubility ($K_{ps}$) that enables it's immediate, ongoing, and residual release over time, maintaining concentrations of copper that allow it to have an antibacterial and/or biocidal effect, but which also are copper concentrations which allow avoidance of the toxicity associated with this compound or excess migration to the food products in contact. In other words, a material with improved antibacterial and/or biocidal effect at lower concentrations of copper is required.

The specific composition of the microparticle of the present invention enables translucent materials to be produced, an important characteristic in the case of food packaging materials, because the particle does not have any carrier to support it and render it bulky gives translucency to the material.

In the case of the present invention, the production of a microparticle of copper which comprises 5 types of copper compounds, each having different solubilities ($K_{ps}$) is proposed. On the one hand, the presence of copper sulfate compounds ($K_{ps}=4\times10^{-36}$), which dissociate instantaneously on contact with moisture—a quick-release copper compound—will make it possible to produce a direct and immediate antibacterial and/or biocidal effect in the material containing it. On the other hand, the presence of copper hydroxide compounds ($K_{ps}=2.2\times10^{-14}$)—a compound with less solubility—will impart to it a bactericidal and/or biocidal effect that is sustained over time. This microparticle offers the advantage that it has the ability to provide 5 different copper compounds, with their own, non-transferable qualities and advantages, which are provided in the same place or physical space upon being introduced into the final polymer or wherever they are placed, providing all of the qualities and advantages of each one of the individual compounds at the same time in the same place and physical space, which is an indispensable condition when low dosages are required, to avoid a loss of translucency and releases of copper that could pass to the products in contact, without diminishing its antibacterial and/or biocidal efficacy, being efficient over time, all in the same place, in a homogeneous form and in contact with foods or other types of products or surfaces where high levels of free circulating copper ions are not required. Thus, the antibacterial and/or biocidal effect of each of the 5 copper compounds can be provided homogenously and at low dosages due to the specific composition of the microparticle according to the present invention.

DETAILED DESCRIPTION OF THE INVENTION

Figure 1:
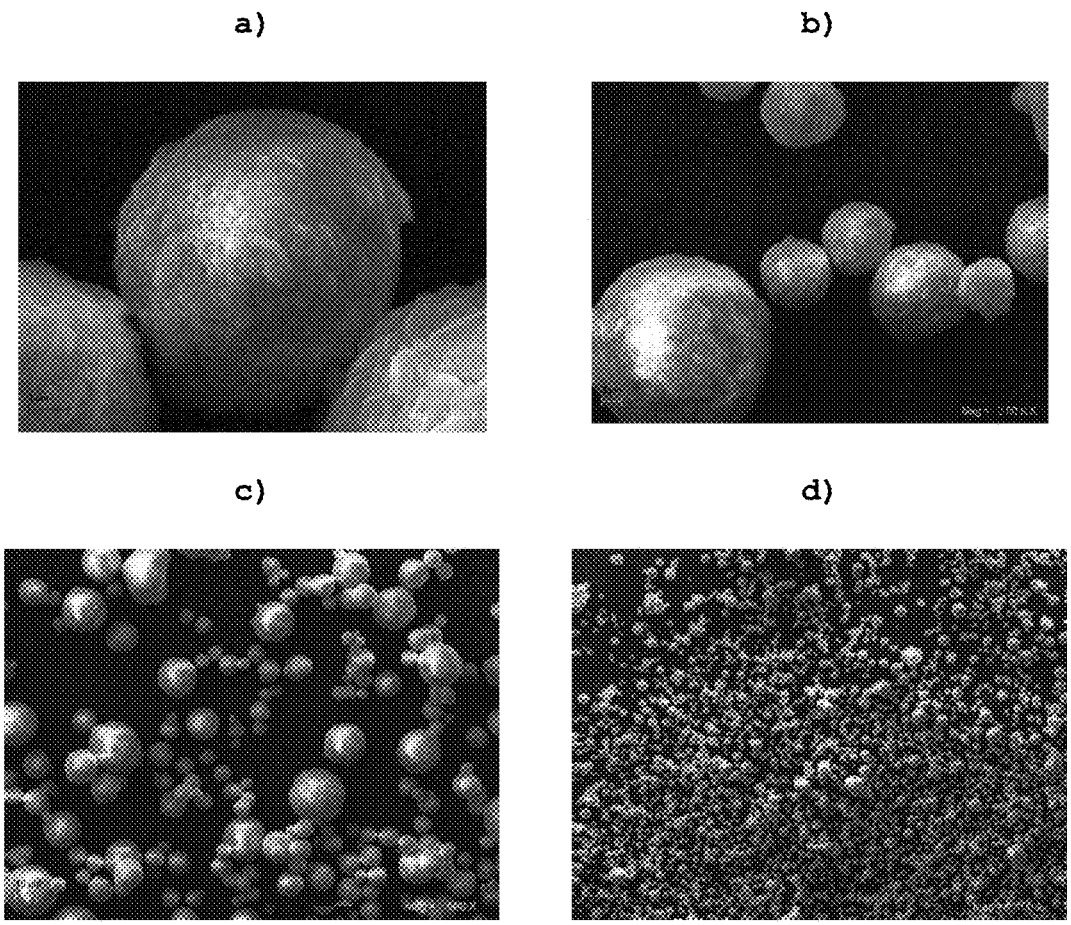
FIG. 1—Scanning electron microscope images of a specimen of copper microparticles of the invention. a) Image obtained at a magnification of 10.00 K X; b) Image at a magnification of 2.50 K X, c) Image at a magnification of 500× y d) Image obtained at a magnification of 100×.

The present invention relates to a microstructured multicomposite copper microparticle that comprises in its composition 5 different types of copper compound: Antlerite $Cu_3^{+2}(SO_4)(OH)_4$, Brochantite $Cu_4^{+2}SO_4(OH)_6$, Chalcantite $Cu^{+2}SO_4.5H_2O$, Natrochalcite $NaCu_2^{+2}(SO_4)_2OH.H_2O$ and Hydrated copper sulfate hydroxide $Cu_3(SO_4)_2(OH)_2.4H_2O/2CuSO_4.Cu(OH)_2.4H_2O$, all regular and crystalline in shape, which give the advantageous structural properties of the microparticles. The microparticle that is part of the scope of the invention has a defined size of between 5 and 50 μm, particularly between 10 and 40, and more particularly between 10 and 15 μm.

The above described microparticle is produced by the means of a method that comprises the following steps:
a) Preparing a solution of solubilized copper sulfate in distilled water in a ratio of 1:10 w/w.
b) Adding to the solution obtained in step a) a 10% w/v sodium hydroxide solution and distilled water until a solution with a pH of between 4 and 6 is obtained.
c) After 24 hours, separating the supernatant and the precipitate which is a copper hydroxide gel;
d) The precipitate in a gel state obtained in step c) is emulsified in a copper sulfate solution in distilled water prepared in a ratio of 1:5 w/v;
e) Subjecting the emulsion obtained in step d) to a drying process, preferably by means of a spray dryer at an inlet temperature of preferably between 220° C. and 280° C. and an outlet temperature of preferably between 80° C. and 100° C.

In carrying out step d) using a dryer of the type spray dryer with the temperatures in the indicated ranges, microparticles are produced in which each of them contains different types of copper compound: Antlerite $Cu_3^{+2}(SO_4)(OH)_4$, Brochantite $Cu_4^{+2}SO_4(OH)_6$, Chalcantite $Cu^{+2}SO_4.5H_2O$, Natrochalcite $NaCu_2^{+2}(SO_4)_2OH.H_2O$ and Hydrated copper sulfate hydroxide $Cu_3(SO_4)_2(OH)_2.4H_2O/2CuSO_4.Cu(OH)_2.4H_2O$, with this not being comparable with a mixture of components or an agglomeration thereof, but rather, on the contrary, being a single microstructured microparticle that comprises the 5 compounds.

The scope of the invention includes a concentrated polymeric composite for use in the plastics industry or in other materials (called masterbatch) that comprises the described copper microparticle and a polymer or resin, which can be included in materials in order to impart antibacterial and/or biocidal activity to them. Particularly but not exclusively, the masterbatch can be utilized in the formation of multilayer sheets having antibacterial and/or biocidal activity.

The technical problem which the present invention intends to resolve is the provision of a novel type of microparticle that comprises 5 types of copper whose regular, crystalline, and microstructured composition enables a controlled release of copper ions that give it antibacterial and/or biocidal properties. The kinetics of the differential release of the 5 different copper compounds included in the microparticle make possible a primary antibacterial and/or biocidal effect on contact and an antibacterial and/or biocidal effect that is sustained over time thanks to the secondary and subsequent release of other kinds of copper present therein. On the other hand, the copper microparticle with these characteristics can form part of a concentrated polymeric composition or masterbatch that can be incorporated during the extrusion process into the molten polymer used to form rigid molds, fibers, filaments, and sheets for the purpose of producing a film, sheet, or structure that incorporates the microparticle and has antibacterial and/or biocidal activity with the technical characteristics and advantages described above.

This structured microparticle can also be used directly or in a mixture to produce an antibacterial and/or biocidal effect in the places in which it is placed.

The targeted placement of the 5 types of copper as part of one and the same microparticle provides substantial technical advantages in terms of its degree of dissociation and release. What is more, the addition of this copper microparticle comprising this multiple composition improves the dispersion of the microparticles, since the Antlerite $Cu_3^{+2}(SO_4)(OH)_4$, Brochantite $Cu_4^{+2}SO_4(OH)_6$, Chalcantite $Cu^{+2}SO_4.5H_2O$, Natrochalcite $NaCu_2^{+2}(SO_4)_2OH.H_2O$ and Hydrated copper sulfate hydroxide $Cu_3(SO_4)_2(OH)_2.4H_2O/2CuSO_4.Cu(OH)_2.4H_2O$ will be present in the same proportions throughout the material, which enables antibacterial and/or biocidal activity to be achieved with advantageously very small doses and with a homogeneous distribution of the 5 types, which also contributes to the translucency of the materials in which they are incorporated, such as in packaging, covering films, or rigid molds, among other things. In addition, all of the compounds that make up the microparticle are in a crystalline form, maintaining an ordered, non-amorphous structure that enables a specific general structure with particular properties to be defined.

The invention also provides for the use of the copper microparticle and of a concentrated polymeric composition (masterbatch) as being useful in the preparation of materials having antibacterial and/or biocidal activity on contact and as a sustained effect. The microstructural configuration of the components comprised by the microparticle allows that when the material comes into contact with bacterial and/or pathogenic agent, it is simultaneously in direct contact with the copper compounds, excercising an immediate antibacterial and/or biocidal effect on contact. The presence of 5 different copper compounds with different solubilities and/or dissociations also enables a sustained effect of the antibacterial and/or biocidal activity of the disclosed microparticle to exist.

When it is noted in the present invention that the material has "biocidal activity," it means that the microparticle is capable of inhibiting the development and growth of bacteria and fungi.

When it is stated that the material has "antibacterial activity," it means that the microparticle inhibits or impedes the proliferation of bacteria.

In the present invention, the term "microstructured" means that the material—the microparticle in this case—consists of a set of phases or components that form it. In the area of materials science, it is said that the microstructure of a material determines its properties.

In the present invention, the term "multicomposite" means that the microparticle comprises at the same time a certain group of different compounds.

The term "masterbatch" refers to a concentrated polymeric composition that comprises a pre-mixture of the elements that will be incorporated into the material to be produced.

The materials that fall within the scope of the invention can include but are not limited to polymers, fibers, fabrics, types of glasses, resins, among others. The polymers include but are not limited to polypropylene (PP), polyethylene (PE), polyethylene terephthalate (PET), ethylene-vinyl acetate (EVA rubber), among others.

In one embodiment of the invention, the microparticle can further comprise other metallic and nonmetallic compounds which have antibacterial action. These compounds include but are not limited to zinc compounds, lead compounds, cadmium compounds, silver compounds, among others.

The exemplary applications presented below illustrate one embodiment of the present invention without limiting the scope thereof.

EXEMPLARY APPLICATIONS

Example 1: Production of Copper Microparticle

The copper hydroxide that makes up the microparticles is prepared by alkalizing a copper sulfate solution containing 100 g/l of pentahydrated copper sulfate, which should produce a completely soluble solution. It is then necessary to dilute sodium hydroxide or another alkali with an OH base to 10% in water; this solution is added slowly and under stirring to the copper sulfate solution that was prepared until a pH of between 4 and 6 is reached, with the following reaction being produced:

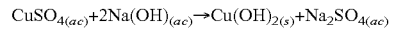

$$CuSO_{4(ac)}+2Na(OH)_{(ac)} \rightarrow Cu(OH)_{2(s)}+Na_2SO_{4(ac)}$$

The reaction produces a precipitate of copper hydroxide in the solution in a gel state, and the supernatant is removed after 24 hours.

The resulting precipitate, which contains copper hydroxide, is emulsified in a copper sulfate solution in a ratio of 1:5. This suspension containing a solubilized ionic phase of copper sulfate and another in gel form such as copper hydroxide is subjected to a drying process using a spray dryer at an inlet temperature of between 220 and 280° C. and outlet temperature of 80° C. to 100° C.

Example 2: Characterization of Copper Microparticle

To characterize the structure, size, and distribution of the copper microparticles produced by means of the protocol described in example 1, a scanning electron microscope (SEM) analysis was performed.

The SEM analysis was performed using the scanning electron microscope (SEM), Zeiss model EVO MA 10 using EDS mode with the Penta FET Precision detector, Oxford Instruments X-act. This analysis consisted in scanning representative specimens of the powder of (solid) copper microparticles and selecting a representative area in order to determine the elemental composition of the microparticle.

Figure 2:
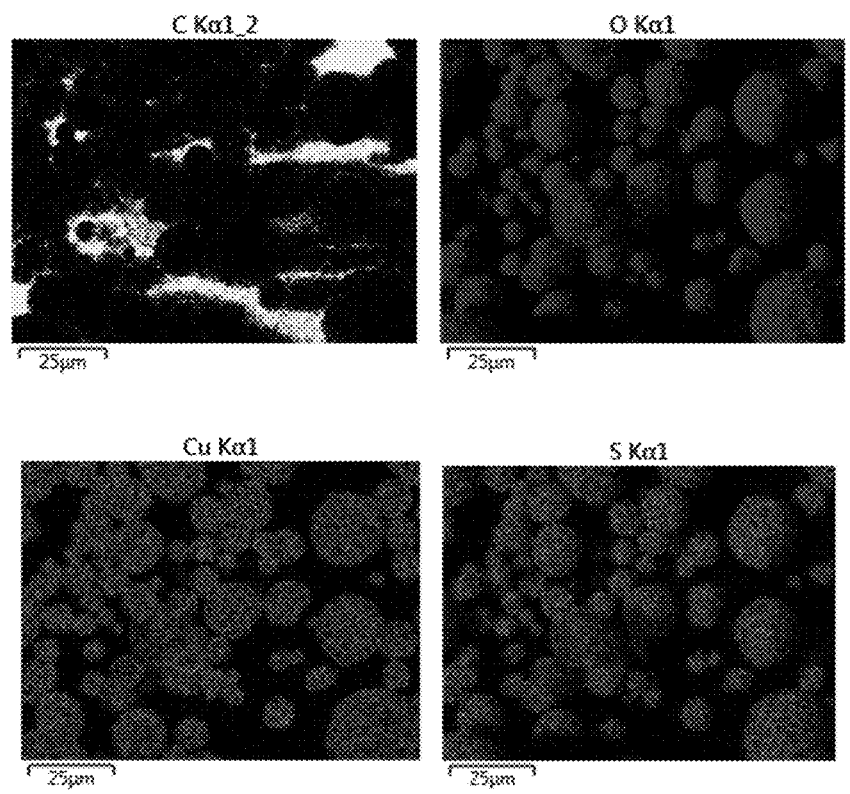
FIG. 2—Determination of elemental composition of copper microparticles of the invention by means of scanning electron microscope coupled with an EDS detector. In a), the result of the mapping of the elements that make up the microparticle is presented: carbon, oxygen, sulfur, and copper; b) shows a diagram of the elemental composition of the copper microparticles of the invention.
Figure 2:
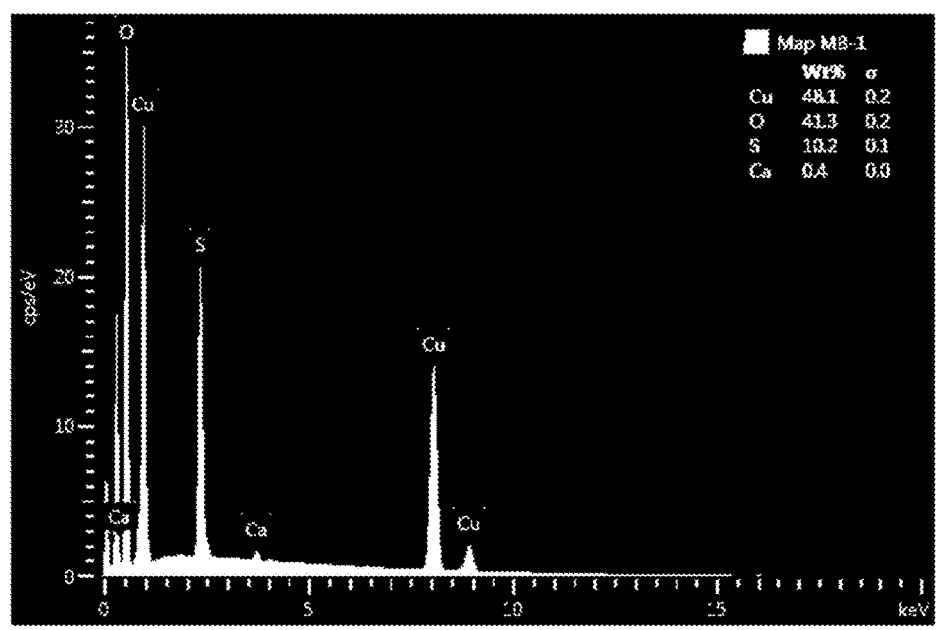

From the SEM images at different magnifications, it was observed that the particle has a regular spherical shape and a heterogeneous size distribution (FIG. 1 *a-d*). By means of the EDS detector that was coupled with the microscope, the elemental composition of the microparticle was determined, and it was established that it is made up of the elements copper, sulfur, and oxygen (FIG. 2 a-d).

With regard to the size of the particles, four independent representative areas of the images taken from two independent specimens of the particles were evaluated. It was determined that the particles have a micrometric size of between 7-22 micrometers (see table 1).

TABLE 1

Representative size of copper particles

|  | Specimen MB-1 (µm) | Specimen MB-2 (µm) |
|---|---|---|
| Measurement 1 | 10.52 | 7.480 |
| Measurement 2 | 19.44 | 10.88 |
| Measurement 3 | 7.61 | 21.94 |
| Measurement 4 | 7.363 | 13.61 |
| Average | 11.23 | 13.48 |

Figure 3:
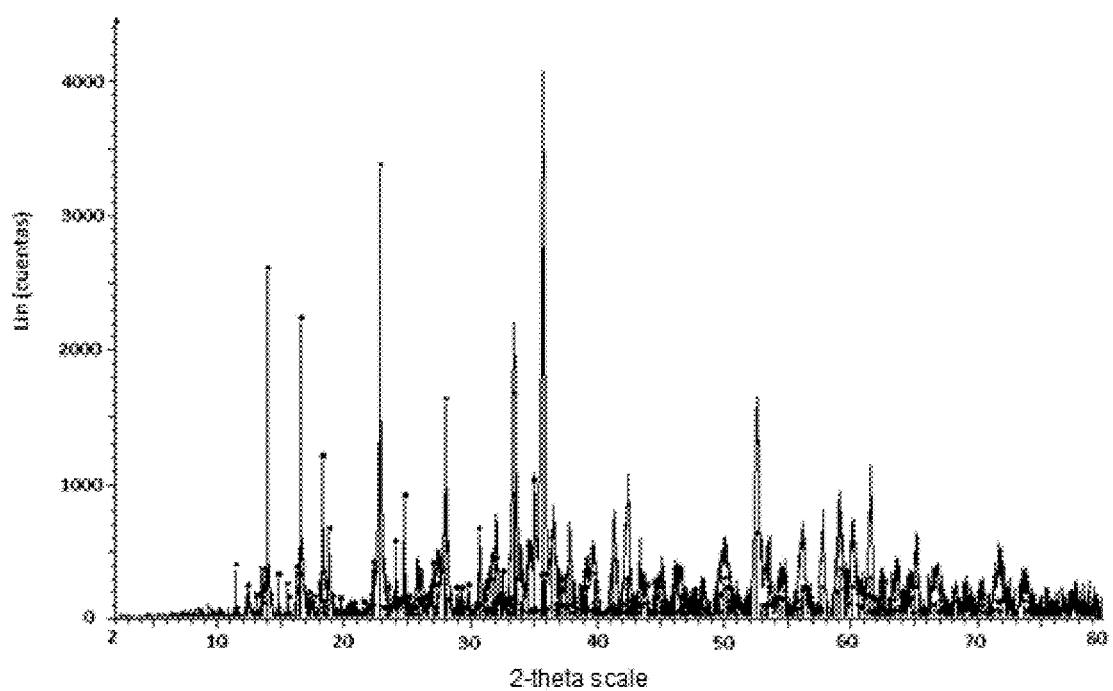
FIG. 3—X-ray diffraction pattern of specimen of copper microparticle of the invention. The difractogram represented by ■ corresponds to antlerite $Cu_3^{+2}(SO_4)(OH)_4$, ● corresponds to brochantite $Cu_4^{+2}SO_4(OH)_6$, ◉ corresponds to chalcantite $Cu^{+2}SO_4.5H_2O$, ▲ corresponds to natrochalcite $NaCu_2^{+2}(SO_4)_2OH.H_2O$, and ▼ corresponds to hydrated copper sulfate hydroxide $Cu_3(SO_4)_2(OH)_2.4H_2O/2CuSO_4.Cu(OH)_2$.

In order to determine the specific chemical composition of the microparticle and to determine the oxidation states of the types of copper contained, an X-ray diffraction analysis was performed. Based on this analysis, an X-ray diffraction pattern was determined by the presence of various compounds (FIG. 3).

In order to define the compounds present in the microparticle, the crystalline powder PDF-2 database was consulted and compared with the pattern obtained. It was determined that the microparticle of the invention is composed of 5 types of copper compound: Antlerite, Brochantite, Chalcantite, Natrochalcite, and Hydrated copper sulfate hydroxide (table 2).

TABLE 2

Chemical composition of copper microparticle

| Name of compound | Chemical structure |
|---|---|
| Antlerite | $Cu_3^{+2}(SO_4)(OH)_4$ |
| Brochantite | $Cu_4^{+2}SO_4(OH)_6$ |
| Chalcantite | $Cu^{+2}SO_4 \cdot 5H_2O$ |
| Natrochalcite | $NaCu_2^{+2}(SO_4)_2OH \cdot H_2O$ |
| Hydrated copper sulfate hydroxide | $Cu_3(SO_4)_2(OH)_2 \cdot 4H_2O/2CuSO_4 \cdot Cu(OH)_2 \cdot 4H_2O$ |

Example 3: Preparation of the Masterbatch. Addition of the Copper Microparticles to Multilayer Polymer Sheets The microparticle described in example 2 can be included in different polymeric materials and resins to form multilayer fibers and sheets. In this example, the protocol followed in preparing the concentrated polymeric composition (masterbatch) and the conditions for the inclusion thereof in resins and polymers are described.

a) Preparation of Concentrated Polymeric Composition (Masterbatch)

To prepare the masterbatch, a premixture of the polymeric material and the microparticle is prepared. For this, the resin or polymeric material is subjected to pulverization in a mill and then cold-mixed with the microparticle.

The premixture is molten at temperatures between 120 and 250° C., depending on the type of resin or polymer: Polypropylene (PP), polyethylene (PE), PET, EVA rubber, and passed through a pellet extruder, which results in a pellet referred to as masterbatch.

b) Inclusion of the Masterbatch in the Process of the Extrusion of Molten Polymer to Form a Multilayer Material.

The masterbatch can be added to the process of the extrusion of molten polymer used to form rigid or flexible polymers such as fibers, filaments, and sheets. The sheets that are produced by means of this procedure can correspond to multilayer structures in which each sheet has a thickness of between 5 and 120 µm, more specifically of between 5 and 30 µm; that is, it is possible to form a final material that can contain 2, 3, and even 5 of these layers of polymeric resins such as PE, PA, PP and/or PET.

Example 4: Antibacterial and/or Biocidal Effect of the Multilayer Polymeric Material with Microstructured Copper Microparticle To evaluate the antibacterial and/or biocidal effect of the multilayer material with microstructured copper microparticles, a test was performed consisting of the addition of a bacterial culture that had been grown previously on the surface of the multilayer material made up of different polymers. The antibacterial and/or biocidal effect on *Escherichia coli* and *Staphylococcus aureus* was evaluated.

The multilayer material was incubated for 24 hours at the temperature required for the growth of bacteria. Once the incubation period had lapsed, a count was performed of the colony-forming units on the material, and this was compared to a material that did not contain copper microparticles. Two types of sheeting were tested depending on the type of polymer added to the masterbatch: 1) sheeting made of polypropylene and copper microparticles (2% w/w added to a masterbatch); and 2) sheeting made of ethylene-vinyl acetate (EVA rubber) with microstructured copper microparticles added into a masterbatch.

The results indicate that, when the colony-forming unit (CFU) count for the sheeting composed of polypropylene and microstructured copper microparticles (2% w/w added to a masterbatch) is compared to the control sheeting that does not include the components of the masterbatch, the sheeting with copper microparticles shows a 99% reduction in the quantity of CFUs, with the bacterial count having been reduced by 3 orders of magnitude (table 3). In the case of the sheeting composed of ethylene-vinyl acetate (EVA rubber) and copper microparticles, an equivalent phenomenon was observed, reflecting a decrease in the CFU count for the bacteria tested on the sheeting that comprises the masterbatch in relation to the control material (table 4).

TABLE 3

Count of colony-forming units on sheeting made of polypropylene and copper microparticles (2% w/w).

| Indicator strain | *Escherichia coli* (CFU) | | *Staphylococcus aureus* (CFU) | |
|---|---|---|---|---|
| Sampling time | 0 h | 24 h | 0 h | 24 h |
| Control material | $1.6 \times 10^5$ | $1.6 \times 10^5$ | $3.6 \times 10^5$ | $3.6 \times 10^5$ |
| Sheeting polypropylene 2% copper masterbatch | — | $2.7 \times 10^2$ | — | $4.3 \times 10^2$ |
| % reduction | — | >99% | — | >99% |

TABLE 4

Count of colony-forming units on sheeting composed of ethylene-vinyl acetate (EVA rubber) and copper microparticles.

| Indicator strain | *Escherichia coli* (CFU) | | *Staphylococcus aureus* (CFU) | |
| --- | --- | --- | --- | --- |
| Sampling time | 0 h | 24 h | 0 h | 24 h |
| Control material | $8.9 \times 10^5$ | $3.3 \times 10^6$ | $5.0 \times 10^5$ | $6.9 \times 10^7$ |
| EVA rubber | — | $2.5 \times 10^2$ | — | $5.6 \times 10^4$ |
| % reduction | — | >99% | — | >99% |

The invention claimed is:

1. A copper microparticle with antibacterial and/or biocidal activity, wherein each microparticle has a regular, crystalline and microstructured composition that comprises 5 different copper compounds: Antlerite $Cu_3^{+2}(SO_4)(OH)_4$, Brochantite $Cu_4^{+2}SO_4(OH)_6$, Chalcantite $Cu^{+2}SO_4 \cdot 5H_2O$, Natrochalcite $NaCu_2^{+2}(SO_4)_2OH \cdot H_2O$ and Hydrated copper sulfate hydroxide $Cu_3(SO_4)_2(OH)_2 4H_2O/2CuSO_4 \cdot Cu(OH)_2$, with the microparticle having a size of between 5 and 50 μm.

2. The copper microparticle with antibacterial and/or biocidal activity as set forth in claim 1, wherein the microparticle has a size of between 10 and 40 μm.

3. The copper microparticle with antibacterial and/or biocidal activity as set forth in claim 1, wherein the microparticle has a size of between 10 and 15 μm.

4. The copper microparticle with antibacterial and/or biocidal activity as set forth in claim 1, wherein it can further comprise other metallic and nonmetallic antibacterial compounds.

5. The copper microparticle with antibacterial and/or biocidal activity as set forth in claim 4, wherein the metallic antibacterial compounds are zinc compounds, lead compounds, cadmium compounds, and silver compounds.

6. The copper microparticle with antibacterial and/or biocidal activity as set forth in claim 4, wherein the metallic antibacterial compounds are zinc compounds, lead compounds, cadmium compounds, and/or silver compounds.

7. A process for preparing copper microparticles with antibacterial and/or biocidal activity as set forth in claim 1, comprising the following steps:
   a) Preparing a solution of solubilized copper sulfate in distilled water in a ratio of 1:10 w/w;
   b) Adding to the solution obtained in step a) a 10% w/v sodium hydroxide solution and distilled water until a solution is obtained that has a pH of between 4 and 6;
   c) After 24 hours, separating the supernatant and the precipitate which is a copper hydroxide gel;
   d) Emulsifying the copper hydroxide gel precipitate of step c) in a copper sulfate solution in distilled water prepared in a ratio of 1:5 w/v;
   e) Subjecting the emulsion obtained in step d) to a drying process; and
   f) Obtaining the copper microparticle according to claim 1, wherein each microparticle has a regular, crystalline and microstructured composition that comprises 5 different copper compounds: Antlerite $Cu_3^{+2}(SO_4)(OH)_4$, Brochantite $Cu_4^{+2}SO_4(OH)_6$, Chalcantite $Cu^{*+2}SO_4 \cdot 5H_2O$, Natrochalcite $NaCu_2^{+2}(SO_4)_2OH \cdot H_2O$ and Hydrated copper sulfate hydroxide $Cu_3(SO_4)_2(OH)_2 4H_2O/2CuSO_4 Cu(OH)_2$.

8. The method according to claim 7, wherein the drying process is by means of a spray dryer.

9. The method according to claim 8, wherein the spray dryer has an inlet temperature between 220° C. and 280° C. and an outlet temperature between 80° C. and 100° C.

10. A concentrated polymeric composition (masterbatch) with antibacterial and/or biocidal activity comprising the copper microparticle as set forth in claim 1 wherein each microparticle has a regular, crystalline and microstructured composition that comprises 5 different copper compounds: Antlerite $Cu_3^{+2}(SO_4)(OH)_4$, Brochantite $Cu_4^{+2}SO_4(OH)_6$, Chalcantite $Cu^{+2}SO_4 \cdot 5H_2O$, Natrochalcite $NaCu_2(SO_4)_2OH \cdot H_2O$ and Hydrated copper sulfate hydroxide $Cu_3(SO_4)_2(OH)_2 4H_2O/2CuSO_4 Cu(OH)_2$, and at least one polymer or resin.

11. The concentrated polymeric composition (masterbatch) as set forth in claim 10, wherein the at least one polymer or resin corresponds to polypropylene (PP), polyethylene (PE), polyethylene terephthalate (PET), ethylene-vinyl acetate (EVA rubber), polystyrene (PS), styrene-butadiene rubber (SBR), polyvinyl chloride (PVC), polytetrafluoroethylene (PTFE), methacrylate (PMMA), polyester, aliphatic polyamides, polyterephthalamides, aramides (aromatic polyamides), rigid and flexible polyurethanes, or silicone.

12. A process for preparation of a concentrated polymeric composition (masterbatch) comprising:
   a) pulverizing a resin or polymeric material;
   b) creating a premixture by cold-mixing the pulverized resin or polymeric material and at least one microparticle according to claim 1 wherein each microparticle has a regular, crystalline and microstructured composition that comprises 5 different copper compounds: Antlerite $Cu_3^{+2}(SO_4)(OH)_4$, Brochantite $Cu_4^{+2}SO_4(OH)_6$, Chalcantite $Cu^{+2}SO_4 \cdot 5H_2O$, Natrochalcite $NaCu_2^{+2}(SO_4)_2OH \cdot H_2O$ and Hydrated copper sulfate hydroxide $Cu_3(SO_4)_2(OH)_2 4H_2O/2CuSO_4 \cdot Cu(OH)_2$;
   c) heating the premixture to a molten state at a temperature between 120 and 250° C.; and
   d) passing the molten premixture through a pellet extruder to obtain a pellet masterbatch.

13. A process for preparation of a fiber, a filament, and/or a sheet having antibacterial activity on contact and with sustained effect comprising
   a) preparing a masterbatch according to claim 12;
   b) adding the masterbatch of step a) to a resin or polymer;
   c) heating the mixture of step b) to a molten state at a temperature between 120 and 250° C.; and
   d) extruding the molten mixture of step c) to form a fiber, a filament, and/or a sheet.

14. The process for preparation of a sheet according to claim 13, wherein the resin or polymer of step b) is selected from the group consisting of polyethylene (PE), polyamide (PA), polypropylene (PP), and/or polyethylene terephthalate (PET).

15. A process for preparation of a multilayer sheet having antibacterial activity on contact and with sustained effect comprising
   a) preparing a masterbatch according to claim 12;
   b) adding the masterbatch of step a) to a resin or polymer;
   c) heating the mixture of step b) to a molten state at a temperature between 120 and 250° C.;
   d) extruding the molten mixture of step c) to form a sheet; and
   e) repeating steps a) to d) at least once,
   f) wherein the extrusion of step e) occurs atop the sheet produced by step d) to produce a multilayer sheet.

* * * * *